(12) United States Patent
Shaber et al.

(10) Patent No.: US 8,563,472 B2
(45) Date of Patent: Oct. 22, 2013

(54) SYNERGISTIC FUNGICIDAL AND ALGICIDAL COMPOSITIONS INCLUDING 2-HYDROXYPHENYLALDEHYDE AND 2-HYDROXYPHENYLKETONE HETEROCYCLOYHYDRAZONES AND COPPER

(75) Inventors: Steven Howard Shaber, Woodbury, NY (US); Gerald Shaber, legal representative, Woodbury, NY (US); Jeffery D. Webster, New Palestine, IN (US); David H. Young, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/212,577

(22) Filed: Aug. 18, 2011

(65) Prior Publication Data
US 2012/0045521 A1 Feb. 23, 2012

Related U.S. Application Data

(60) Provisional application No. 61/375,284, filed on Aug. 20, 2010.

(51) Int. Cl.
*A01N 59/16* (2006.01)
*A01N 55/02* (2006.01)
*A61K 31/555* (2006.01)

(52) U.S. Cl.
USPC .......................... 504/121; 504/191; 514/184

(58) Field of Classification Search
None
See application file for complete search history.

(56) References Cited

U.S. PATENT DOCUMENTS 4,277,500 A * 7/1981 Rusay .......................... 514/615
5,173,276 A * 12/1992 Kruesi ........................... 423/23

* cited by examiner

*Primary Examiner* — Alton Pryor
(74) *Attorney, Agent, or Firm* — C. W. Arnett

(57) ABSTRACT

The present invention relates to the use of mixtures containing 2-hydroxyphenylaldehyde and 2-hydroxyphenylketone heterocycloylhydrazone compounds and copper for controlling the growth of fungi and algae.

17 Claims, No Drawings

SYNERGISTIC FUNGICIDAL AND ALGICIDAL COMPOSITIONS INCLUDING 2-HYDROXYPHENYLALDEHYDE AND 2-HYDROXYPHENYLKETONE HETEROCYCLOYHYDRAZONES AND COPPER

CROSS REFERENCE TO RELATED APPLICATIONS

This application claims the benefit of U.S. Provisional Patent Application Ser. No. 61/375,284 filed Aug. 20, 2010, which is expressly incorporated by reference herein.

FIELD OF THE INVENTION

The present invention relates to the use of hydrazones in combination with copper, copper-based fungicides, copper-based algicides or other copper-containing materials as synergistic fungicidal or algicidal mixtures.

BACKGROUND

Copper is used to control the growth of organisms, especially microorganisms, in a variety of applications such as those described in the *Handbook of Copper Compounds and Applications*, edited by H. W. Richardson and published by Marcel Dekker, Inc. New York (1997), which is expressly incorporated by reference herein. These applications may include its use in agriculture to control a wide range of fungal and bacterial diseases of plants. Copper products may also be used as aquatic biocides in fresh or marine environments. Copper products may be used in antifouling applications and to control unwanted organisms in ponds and lakes based on the toxicity of copper towards algae, fungi, macrophytes and mollusks. Copper-based materials may also be used as wood preservatives and on other materials to inhibit fungal and bacterial growth. Other uses also include killing plant roots in sewer systems.

Ecological risk assessment studies have shown that copper products, which normally are applied at high use rates, may be toxic to birds, mammals, fish and other aquatic species ("Reregistration Eligibility Decision (RED) for Coppers," EPA 738-R-06-020, July 2006, which is expressly incorporated by reference herein). Thus, while copper is a highly useful agent for controlling the growth of undesirable organisms in different environments, it is desirable to minimize the amount of copper applied.

SUMMARY OF THE INVENTION

One exemplary embodiment of the present disclosure includes a synergistic mixture for controlling the growth of fungi and algae, the synergistic mixture including copper and a hydrazone compound of Formula I:

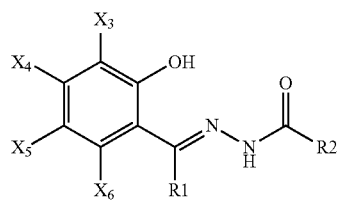

Formula I $R_1$ is H, or $C_1$-$C_6$ alkyl;

$R_2$ is a substituted or unsubstituted 5- or 6-membered aromatic, saturated, or partially saturated heterocyclic ring whose members consist of carbon and at least one other atom chosen from O, N, or S which may optionally be fused with a second substituted or unsubstituted 5- or 6-membered aromatic, saturated, or partially saturated ring whose members consist of carbon or whose members consist of carbon and one or more other atoms chosen from O, N, or S;

$X_3$ is H, halogen, or $C_2$-$C_6$ alkenyl;

$X_4$ is H;

$X_5$ is H or halogen; and $X_6$ is H;

with the proviso that $X_5$ and $X_6$ may form a 6-membered aromatic fused ring consisting of carbon and hydrogen.

The term "alkyl" refers to a branched, unbranched, or cyclic carbon chain, including methyl, ethyl, propyl, butyl, isopropyl, isobutyl, tertiary butyl, pentyl, hexyl, cyclopropyl, cyclobutyl, cyclopentyl, cyclohexyl and the like.

The term "cycloalkyl" refers to a monocyclic or polycyclic, saturated substituent consisting of carbon and hydrogen.

The term "alkenyl" refers to a branched, unbranched or cyclic carbon chain containing one or more double bonds including ethenyl, propenyl, butenyl, isopropenyl, isobutenyl, cyclohexenyl, and the like.

The term "alkynyl" refers to a branched or unbranched carbon chain containing one or more triple bonds including propynyl, butynyl and the like.

As used throughout this specification, the term 'R' refers to the group consisting of $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$ haloalkenyl, $C_2$-$C_6$ haloalkynyl, or $C_3$-$C_6$ halocycloalkyl, unless stated otherwise.

The term "alkoxy" refers to an —OR substituent.

The term "alkylthio" refers to an —SR substituent.

The term "haloalkylthio" refers to an alkylthio, which is substituted with Cl, F, I, or Br or any combination thereof.

The term "cyano" refers to a —C≡N substituent.

The term "hydroxyl" refers to an —OH substituent.

The term "haloalkoxy" refers to an —OR—X substituent, wherein X is Cl, F, Br, or I, or any combination thereof.

The term "haloalkyl" refers to an alkyl, which is substituted with Cl, F, I, or Br or any combination thereof.

The term "halocycloalkyl" refers to a monocyclic or polycyclic, saturated substituent consisting of carbon and hydrogen, which is substituted with Cl, F, I, or Br or any combination thereof.

The term "haloalkenyl" refers to an alkenyl, which is substituted with Cl, F, I, or Br or any combination thereof.

The term "haloalkynyl" refers to an alkynyl which is substituted with Cl, F, I, or Br or any combination thereof.

The term "halogen" or "halo" refers to one or more halogen atoms, defined as F, Cl, Br, and I.

The term "aryl" refers to a cyclic, aromatic substituent consisting of hydrogen and carbon.

The term "heteroaryl" refers to a cyclic substituent that may be fully unsaturated, where the cyclic structure contains at least one carbon and at least one heteroatom, where said heteroatom is nitrogen, sulfur, or oxygen.

The term "phenoxy" refers to an —O substituted with a six-membered fully unsaturated ring consisting of hydrogen and carbon.

The term "nitro" refers to a —NO₂ substituent.

The term "benzyl" refers to a —CH₃ substituted with a six-membered fully unsaturated ring consisting of hydrogen and carbon.

The term "benzoyl" refers to a carbonyl substituted with a six-membered fully unsaturated ring consisting of hydrogen and carbon.

The term "heterocyclic ring" refers to a cyclic structure that may be fully or partially saturated or fully unsaturated, where the cyclic structure contains at least one carbon and at least one heteroatom, where said heteroatom is nitrogen, sulfur, or oxygen.

The term "azido" refers to a —$N_3$ substituent.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric or tautomeric forms of the molecule.

Additional features and advantages of the present invention will become apparent to those skilled in the art upon consideration of the following detailed description of the illustrative embodiments exemplifying the best mode of carrying out the invention as presently perceived.

DETAILED DESCRIPTION OF THE DISCLOSURE

The embodiments of the invention described herein are not intended to be exhaustive or to limit the invention to the precise forms disclosed. Rather, the embodiments selected for description have been chosen to enable one skilled in the art to practice the invention. Although the disclosure is described as a synergistic combination of copper, copper-based fungicides, copper-based algicides or other copper-containing materials and a hydrazone or hydrazone derivative it should be understood that the concepts presented herein may be used in various applications and should not be limited.

The mixtures of the present invention have fungitoxic activity against phytopathogenic fungi, against fungal pathogens of mammals, including humans, and against wood decay causing fungi. The mixtures of the present invention may have broad spectrum fungitoxic activity, particularly against phytopathogenic fungi. They are active against fungi of a number of classes including Deuteromycetes (Fungi Imperfecti), Basidiomycetes, Oomycetes and Ascomycetes. More particularly, the method of this invention provides for activity against organisms including, but not limited to, *Phytophthora* species, *Plasmopara viticola, Pseudoperonospora cubensis, Pythium* species, *Pyricularia oryzae, Colletotrichum* species, *Helminthosporium* species, *Alternaria* species, *Septoria nodorum, Leptosphaeria nodorum, Ustilago maydis, Erysiphe graminis, Puccinia* species, *Sclerotinia* species, *Sphaerotheca fuliginea, Cercospora* species, *Rhizoctonia* species, *Uncinula necator, Septoria tritici*, and *Podosphaera leucotricha*.

The method of the present invention also provides for activity against fungal pathogens of mammals (including humans) including, but not limited to, *Candida* species such as *C. albicans, C. glabrata, C. parapsilosis, C. krusei*, and *C. tropicalis, Aspergillus* species such as *Aspergillus fumigatus, Fusarium* species, *Coccidioides immitis, Cryptococcus neoformans, Histoplasma capsulatum, Microsporum* species, and *Tricophyton* species. The method of the present invention also provides for activity against fungi which cause wood decay such as *Gleophyllum trabeur, Phialophora mutabilis, Poria palcenta* and *Trametes versicolor*.

The present invention contemplates all vehicles by which the composition of the present invention can be formulated for delivery and use as a pesticide composition, including solutions, suspensions, emulsions, wettable powders and water dispersible granules, emulsifiable concentrates, granules, dusts, baits, and the like. Typically, formulations are applied following dilution of the concentrated formulation with water as aqueous solutions, suspensions or emulsions, or combinations thereof. Such solutions, suspensions or emulsions are produced from water-soluble, water-suspended or water-suspendable, water-emulsified or water-emulsifiable formulations or combinations thereof which are solids, including and usually known as wettable powders or water dispersible granules; or liquids including and usually known as emulsifiable concentrates, aqueous suspensions or suspension concentrates, and aqueous emulsions or emulsions in water, or mixtures thereof such as suspension-emulsions. As will be readily appreciated, any material to which this composition can be added may be used, provided they yield the desired utility without significant interference with the desired activity of the pesticidally active ingredients as pesticidal agents and improved residual lifetime or decreased effective concentration is achieved.

Wettable powders, which may be compacted to form water dispersible granules, comprise an intimate mixture of one or more of the pesticidally active ingredients, an inert carrier and surfactants. The concentration of the pesticidally active ingredient in the wettable powder is usually from about 10 percent to about 90 percent by weight based on the total weight of the wettable powder, more preferably about 25 weight percent to about 75 weight percent. In the preparation of wettable powder formulations, the pesticidally active ingredients can be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the pesticidally active ingredient comprise a convenient concentration, such as from about 10 weight percent to about 50 weight percent of the pesticidally active ingredient, in a suitable liquid, based on the total weight of the concentrate. The pesticidally active ingredients are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters esterified with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts of sulfated polyglycol ethers and appropriate salts of phosphated polyglycol ether.

Representative organic liquids which can be employed in preparing emulsifiable concentrates are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides; and glycol ethers such as the n-butyl ether, ethyl ether or methyl ether of diethylene glycol, and the methyl ether of triethylene glycol and the like. Mixtures of two or more organic liquids may also be employed in the preparation of the emulsifiable concentrate. Surface-active emulsifying agents are typically employed in liquid formulations and in an amount of from 0.1 to 20 percent by weight based on the combined weight of the emulsifying agents. The formulations can also contain other compatible additives, for example, plant growth regulators and other biologically active compounds used in agriculture.

Aqueous suspensions comprise suspensions of one or more water-insoluble pesticidally active ingredients dispersed in an aqueous vehicle at a concentration in the range from about 5 to about 50 weight percent, based on the total weight of the aqueous suspension. Suspensions are prepared by finely grinding one or more of the pesticidally active ingredients, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 50 weight percent, based on the total weight of the aqueous emulsion. If the pesticidally active ingredient is a solid it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compositions of the present invention can also be granular formulations, which are particularly useful for applications to the soil. Granular formulations usually contain from about 0.5 to about 10 weight percent, based on the total weight of the granular formulation of the pesticidally active ingredient(s), dispersed in an inert carrier which consists entirely or in large part of coarsely divided inert material such as attapulgite, bentonite, diatomite, clay or a similar inexpensive substance. Such formulations are usually prepared by dissolving the pesticidally active ingredients in a suitable solvent and applying it to a granular carrier which has been preformed to the appropriate particle size, in the range of from about 0.5 to about 3 mm A suitable solvent is a solvent in which the compound is substantially or completely soluble. Such formulations may also be prepared by making a dough or paste of the carrier and the compound and solvent, and crushing and drying to obtain the desired granular particle.

Dusts can be prepared by intimately mixing one or more of the pesticidally active ingredients in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the pesticidally active ingredients onto the target site such as a crop or organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters of sulfosuccinic acids, ethoxylated organosilicones, ethoxylated fatty amines and blends of surfactants with mineral or vegetable oils.

The formulations may optionally include combinations that contain other pesticidal compounds. Such additional pesticidal compounds may be fungicides, insecticides, nematocides, miticides, arthropodicides, bactericides or combinations thereof that are compatible with the mixtures of the present invention in the medium selected for application, and not antagonistic to the activity of the present mixtures. Accordingly, in such embodiments, the other pesticidal compound is employed as a supplemental toxicant for the same or for a different pesticidal use. The mixtures of the present invention and the pesticidal compound in the combination can generally be present in a weight ratio of from 1:100 to 100:1.

For pharmaceutical use, the mixtures described herein may be taken up in pharmaceutically acceptable carriers, such as, for example, solutions, suspensions, tablets, capsules, ointments, elixirs and injectable compositions. Pharmaceutical preparations may contain from 0.1% to 99% by weight of active ingredient. Preparations which are in single dose form, "unit dosage form," preferably contain from 20% to 90% active ingredient, and preparations which are not in single dose form preferably contain from 5% to 20% active ingredient. As used herein, the term "active ingredient" refers to mixtures described herein, salts thereof, hydrates, and mixtures with other pharmaceutically active compounds. Dosage unit forms such as, for example, tablets or capsules, typically contain from about 0.05 to about 1.0 g of active ingredient.

The mixtures of the present invention can also be combined with other agricultural fungicides to form fungicidal mixtures and synergistic mixtures thereof. The fungicidal mixtures of the present invention are often applied in conjunction with one or more other fungicides to control a wider variety of undesirable diseases. When used in conjunction with other fungicide(s), the presently claimed mixtures can be formulated with the other fungicide(s), tank mixed with the other fungicide(s) or applied sequentially with the other fungicide(s). Such other fungicides include amisulbrom 2-(thiocyanatomethylthio)-benzothiazole, 2-phenylphenol, 8-hydroxyquinoline sulfate, antimycin, Ampelomyces, quisqualis, azaconazole, azoxystrobin, *Bacillus subtilis, Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, boscalid, bromuconazole, bupirimate, BYF 1047, calcium polysulfide, captafol, captan, carbendazim, carboxin, carpropamid, carvone, chlazafenone, chloroneb, chlorothalonil, chlozolinate, *Coniothyrium minitans*, cyazofamid, cyflufenamid, cymoxanil, cyproconazole, cyprodinil, coumarin, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mepanipyrim, mepronil, meptyl-dinocap, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, silthiofam, simeconazole, sodium 2-phenylphenoxide, sodium bicarbonate, sodium pentachlorophenoxide, spiroxamine, sulfur, SYP-Z071, SYP-048, SYP-Z048, tar oils, tebuconazole, tecnazene, tetraconazole, thiabendazole, thifluzamide, thiophanate-methyl, thiram, tiadinil, tolclofos-methyl, tolylfluanid, triadimefon, triadimenol, triazolopyrimidine, triazoxide, tricyclazole, tridemorph, trifloxystrobin, triflumizole, triforine, triticonazole, validamycin, vinclozolin, zineb, ziram, zoxamide, *Candida oleophila, Fusarium cocysporum, Gliocladium* spp., *Phlebiopsis gigantean, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, 5-fluorocytosine and profungicides thereof, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenyl-itaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, picolinamide UK-2A and derivatives thereof, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thi-cyofen, thiochlorfenphim, thiophanate, thioquinox, tioxymid, triamiphos, triarimol, triazbutil, trichlamide, urbacid, zarilamide, and any combinations thereof.

The mixtures of the present invention can also be combined with other antifungal compounds used to control infections in mammals to form fungicidal mixtures and synergistic mixtures thereof. The fungicidal mixtures of the present invention can be applied in conjunction with one or more other antifungal compounds or their pharmaceutically acceptable salts to control a wider variety of undesirable diseases. When used in conjunction with other antifungal compounds, the presently claimed mixtures can be formulated with the other antifungal compound(s), coadministered with the other antifungal compound(s) or applied sequentially with the other antifungal compound(s). Typical antifungal compounds include, but are not limited to compounds selected from the group consisting of an azole such as fluconazole, voriconazole, itraconazole, ketoconazole, and miconazole, a polyene such as amphotericin B, nystatin or liposomal and lipid forms thereof such as Abelcet, AmBisome and Amphocil, a purine nucleotide inhibitor such as 5-fluorocytosine, a polyoxin such as nikkomycin, and pneumocandin or echinocandin derivatives such as caspofungin and micofungin.

Additionally, the mixtures of the present invention can be combined with other pesticides, including insecticides, nematocides, miticides, arthropodicides, bactericides or combinations thereof that are compatible with the mixtures of the present invention in the medium selected for application, and not antagonistic to the activity of the present mixtures to form pesticidal mixtures and synergistic mixtures thereof. The fungicidal mixtures of the present invention are often applied in conjunction with one or more other pesticides to control a wider variety of undesirable pests. When used in conjunction with other pesticides, the presently claimed mixtures can be formulated with the other pesticide(s), tank mixed with the other pesticide(s) or applied sequentially with the other pesticide(s). Typical insecticides include, but are not limited to: antibiotic insecticides such as allosamidin and thuringiensin; macrocyclic lactone insecticides such as spinosad; avermectin insecticides such as abamectin, doramectin, emamectin, eprinomectin, ivermectin and selamectin; milbemycin insecticides such as lepimectin, milbemectin, milbemycin oxime and moxidectin; arsenical insecticides such as calcium arsenate, copper acetoarsenite, copper arsenate, lead arsenate, potassium arsenite and sodium arsenite; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxy-carboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, paradichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as .alpha.-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethyl-amine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoate-methyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, cyenopyrafen, ethiprole, fipronil, flufiprole, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cycloprothrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, meperfluthrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tetramethylfluthrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; tetronic acid insecticides such as spiromesifen; thiourea insecticides such as diafenthiuron; urea insecticides such as flucofuron and sulcofuron; and unclassified insecticides such as closantel, crotamiton, EXD, fenazaflor, fenoxacrim, flubendiamide, hydramethylnon, isoprothiolane, malonoben, metaflumizone, metoxadiazone, nifluridide, pyridaben, pyridalyl, rafoxanide, triarathene, triazamate, meptyldinocap, pyribencarb and any combinations thereof.

The mixtures have broad ranges of efficacy as fungicides. The exact amounts of hydrazones and copper-containing materials to be applied is dependent not only on the specific materials being applied and relative amounts of hydrazone and copper in the mixtures, but also on the particular action desired, the fungal species to be controlled, and the stage of growth thereof, as well as the part of the plant or other product to be contacted with the mixture. Thus, all the mixtures, and formulations containing the same, may not be equally effective at similar concentrations or against the same fungal species.

The mixtures are effective in use with plants in a disease-inhibiting and phytologically acceptable amount. The term "disease inhibiting and phytologically acceptable amount" refers to an amount of a mixture that kills or inhibits the plant disease for which control is desired, but is not significantly toxic to the plant. The exact amount of a mixture required varies with the fungal disease to be controlled, the type of formulation employed, the method of application, the particular plant species, climate conditions, and the like. The dilution and rate of application will depend upon the type of equipment employed, the method and frequency of application desired and diseases to be controlled. For foliar control of fungal infections on plants, the amount of copper used in mixture with hydrazone may range from 0.001 to 5 kilograms per hectare (kg/ha), and preferably from 0.05 to 1 kg/ha. The amount of hydrazone used in mixture with copper may range from 0.001 to 5 kg/ha, and preferably from 0.05 to 1 kg/ha. The molar ratio of copper to hydrazone may range from 0.1:1 to 10,000:1, preferably from 0.5:1 to 1000:1 and more preferably from 1:1 to 20:1.

It should be understood that the preferred amount of a copper material to be mixed with hydrazone in a given application may be influenced by availability of copper from other sources such as copper present in the soil or irrigation water, copper present on the foliage from natural sources, copper applied for fungal or bacterial disease control, copper applied as a fertilizer component, copper present in the water used in preparing fungicide solutions for application such as in spray application, copper present in formulations used in preparing spray solutions or dusts for application, or any other suitable copper source.

For fungal control the hydrazone may be applied before or after the application of copper such that the mixture is generated in the location where fungal control is desired. Additionally, multiple applications of copper or the hydrazone may be applied.

As a seed protectant, the amount of toxicant coated on the seed is usually at a dosage rate of about 10 to about 250 grams (g) and preferably from about 20 to about 60 g per 50 kilograms (kg) of seed. As a soil fungicide, the chemical can be incorporated in the soil or applied to the surface usually at a rate of 0.5 to about 20 kg and preferably about 1 to about 5 kg/ha.

The mixtures of the present invention may have broad spectrum algicidal activity. Algae which may be controlled by the method of the present invention include individual species and mixed cultures. Examples of species controlled include green algae such as *Chlamydomonas reinhardtii, Chlorella pyrenoidosa, Scenedesmus quadricauda, Chlorococcum oleofaciens*, and *Selenastrum* species; blue-green algae (cyanobacteria) such as *Phormidium* species, *Anabaena flosaquae, Nostoc commune, Osiffiatorae* species, *Synechocystis* species, and *Synechococcus* species; and marine algae such as *Dunaliella parva*.

According to the method of the present invention, the mixtures described herein may be combined with other known antialgal compounds including: chlorine/bromine compounds, glutaraldehyde, isothiazoles, isothiazolones, organotin formulations, quaternary ammonium compounds, and triazines.

The amount of the active mixture required to control algae will depend upon many factors such as, for example: the type of surface; the amount of water present; whether the active mixture is incorporated into a coating composition, applied directly to an object, or added to an aqueous or other solution; and the type and extent of algal infestation.

While the mixtures described herein may be administered alone to control algae, it is preferable to administer them as formulations. Useful formulations comprise one or more compounds and one or more acceptable carriers. The term "acceptable carrier" means a carrier compatible with the active mixture and other ingredients of the formulation and which is not toxic to the system or which will not cause degradation of the system. Formulations of the mixtures may contain from 0.01 to 99.9 percent by weight of the mixture. More typically the solutions and formulations will contain from 1.0 to 85 percent by weight of the mixture. Useful formulations include aqueous solutions, solvent based solutions, wettable powders, emulsifiable concentrates, dusts, granular formulations, pellets, aerosols, or flowable emulsion concentrates. In such formulations, the compounds are extended with liquid or solid carriers and, when desired, suitable surfactants are incorporated.

In the case of spray formulations, it is often desirable to include one or more adjuvants, such as wetting agents, spreading agents, dispersing agents, stickers, adhesives, emulsifying agents and the like. Such adjuvants commonly used in the art can be found in the John W. McCutcheon, Inc. publication *Detergents and Emulsifiers, Annual*, Allured Publishing Company, Ridgewood, N.J., U.S.A. Spray formulations can be administered using common application methods, such as conventional high-volume hydraulic sprays, low-volume sprays, air-blast spray, aerial sprays, backpack and hand held sprays, and dusts. The dilution and rate of application will depend upon the type of equipment employed, the method of application, area treated, and algae to be controlled.

The mixtures of the present invention may also be used to control algae in cooling tower waters. In such applications the hydrazone and copper components of the mixtures are maintained at a concentration of from 0.001 ppm to the solubility limit of the compound, preferably 0.01 to 200 ppm.

In addition, the compounds of the present invention are useful for imparting algal resistance to coatings or impregnated compositions. In such applications, the mixtures are incorporated into the coating or into the impregnating composition at a concentration from 0.1 to 10 percent by weight, preferably 1 to 5 percent by weight.

The compounds of the present invention may also be useful for imparting algal resistance to construction products such as stucco, roof mastics, wall mastics, and masonry coatings; in clear finishes and coatings to protect underlying substrates from algae; for algae control in aquaculture including aquaria, fish hatcheries, shrimp ponds, finfish ponds, mollusk and crustacean cultivation; for algae control in recreational and decorative bodies of water such as swimming pools, lakes, fountains, and decorative ponds; for algae control in bodies of water for industrial or municipal use, such as settling or separation ponds, waste treatment ponds, and water reservoirs; for algae control in hydroponic farming or rice paddies; for algae control in processing and manufacture of pulp and paper products; and for inclusion in plastics or in coatings for plastics to protect against algae. Care must be taken in the selection of compound and application rate to avoid adverse effects on non-target organisms.

The mixtures have broad ranges of efficacy as algicides. The exact amounts of hydrazones and copper-containing materials to be applied is dependent not only on the specific materials being applied and relative amounts of hydrazone and copper in the mixtures, but also on the particular action desired, the algal species to be controlled, and the stage of growth thereof, as well as the location to be contacted with the mixture. Thus, all the mixtures, and formulations containing the same, may not be equally effective at similar concentrations or against the same algal species.

The exact amount of a mixture required varies with the algal species to be controlled, the type of formulation employed, the method of application, climate conditions, and the like. The dilution and rate of application will depend upon the type of equipment employed, the method and frequency of application desired and algal species to be controlled. The molar ratio of copper to hydrazone in the active mixture may range from 0.1:1 to 10,000:1, preferably from 0.5:1 to 1000:1 and more preferably from 1:1 to 20:1.

It should be understood that the preferred amount of a copper material to be mixed with hydrazone in a given application may be influenced by availability of copper from other sources such as copper present in the body of water or material to be treated, copper present in the water or solvent used in preparing the algicidal solutions for application such as in spray application, copper present in formulations used in preparing spray solutions or dusts for application, or any other suitable copper source.

For algal control the hydrazone may be applied before or after the application of copper such that the mixture is generated in the location where control is desired. Additionally, multiple applications of copper or the hydrazone may be applied.

As exemplified below, hydrazones of the present invention, or their metal complexes, in a mixture with inorganic or organic mono- or divalent copper salts or chelates (hereinafter referred to as "copper products") increase the biological potency of copper products, enabling comparable or improved efficacy at lower copper use rates. While not intending to be all-inclusive, copper products which may be mixed with the compounds of the present invention to provide enhanced potency may include the following: copper oxychloride, copper octanoate, copper ammonium carbonate, copper arsenate, copper oxysulfate, copper formate, copper propionate, copper oxyacetate, copper citrate, copper chloride, copper diammonium chloride, copper nitrate, copper carbonate, copper phosphate, copper pyrophosphate, copper disodium EDTA, copper diammonium EDTA, copper oxalate, copper tartrate, copper gluconate, copper glycinate, copper glutamate, copper aspartate, copper adipate, copper palmitate, copper stearate, copper caprylate, copper decanoate, copper undecylenate, copper neodecanoate, copper linoleate, copper oleate, copper borate, copper methanesulfonate, copper sulfamate, copper acetate, copper hydroxide, copper oxide, copper oxychloride-sulfate, copper sulfate, basic copper sulfate, copper-oxine, copper 3-phenylsalicylate, copper chloride hydroxide, copper dimethyldithiocarbamate, ammonium copper sulfate, copper magnesium sulfate, copper naphthenate, copper ethanolamine, chromated copper arsenate, ammoniacal copper arsenate, ammoniacal copper zinc arsenate, ammoniacal copper borate, Bordeaux mixture, copper zinc chromate, cufraneb, cupric hydrazinium sulfate, cuprobam, nano-copper materials, copper didecyldimethylammonium chloride, Algimycin P11-C, Aquatrine, A&V-70, Cutrine-plus, Stocktrine II and K-Tea algicide and where appropriate the hydrates of such compounds.

Methods for preparation of salicylaldehyde benzoylhydrazones and 2-hydroxyphenylketone benzoylhydrazones from salicylaldehydes or 2-hydroxyphenyl ketones and benzoic acid hydrazides are well known in the literature. These methods are readily adaptable to the preparation of 2-hydroxyphenylaldehyde and 2-hydroxyphenylketone heterocycloylhydrazones by the substitution of an appropriate heterocyclic carboxylic acid hydrazide for the benzoic acid hydrazide starting material. In addition the preparation of metal complexes of these materials is also well known (see for example Ainscough et al. *J. Inorg. Biochem.* 1999, 77, 125-133, which is expressly incorporated by reference herein). The preparation of 2-hydroxyphenylaldehyde and 2-hydroxyphenylketone heterocycloylhydrazones from salicylaldehydes or 2-hydroxyphenyl ketones and a heterocyclic carboxylic acid hydrazide is also well documented (see, for example, Vergara et al. *J. Med. Chem.* 2009, 44, 4954-4959; Gupta et al. *Polyhedron* 2009, 28, 3577-3585; and Gadre et al. *Indian J. Chem., Sect. B* 2007, 46B, 653-9, which are expressly incorporated by reference herein).

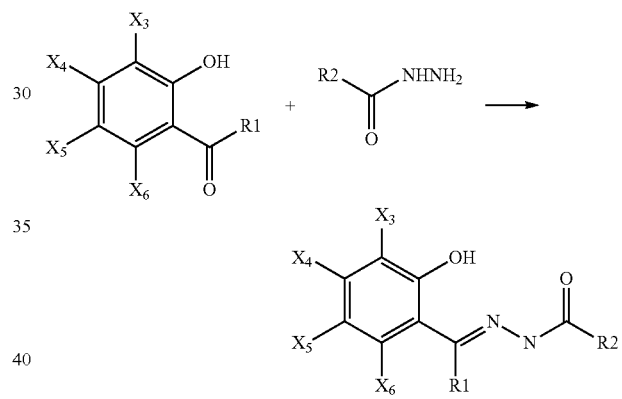

Methods of preparation of the precursor hydrazides are also well known. Hydrazides can be prepared, for example, from carboxylic acids such as in Maxwell et al. *J. Med. Chem.* 1984, 27, 1565-1570 or as in Ramalakshmi et al. *Int. J. Chem. Sci.* 2008, 6, 1213-1222, which are expressly incorporated by reference herein. They may also be prepared from carboxylic esters such as in Dydio et al. *J. Org. Chem.* 2009, 74, 1525-1530 or as in Chary et al. *Sulfur Letters,* 1988, 8, 79-88, which are expressly incorporated by reference herein.

Thus, the synthesis of any 2-hydroxyphenylaldehyde or 2-hydroxyphenylketone heterocycloylhydrazone of Formula I and its metal complex(es) is fully described where the starting aldehyde or ketone, and the starting heterocyclic hydrazide, acid, or ester are described or commercially available.

The hydrazones disclosed may also be in the form of pesticidally acceptable salts and hydrates.

The compounds of Formula I may, therefore, be made using well-known chemical procedures. Intermediates not specifically mentioned in this disclosure are either commercially available, may be made by routes disclosed in the chemical literature, or may be readily synthesized from commercial starting materials utilizing standard procedures.

The following examples are presented to illustrate the various aspects of the compounds of the present disclosure and should not be construed as limitations to the claims.

General Method A

Preparation of 2-hydroxyphenylaldehyde and 2-hydroxyphenylketone heterocycloylhydrazones from 2-hydroxyphenylaldehydes or 2-hydroxyphenylketones and a heterocyclic carboxylic acid hydrazide A 2-hydroxyphenylaldehyde or 2-hydroxyphenylketone is agitated together in a suitable solvent, such as ethyl alcohol (EtOH) with or without the addition of up to 10% acetic acid (HOAc), with an equimolar amount of a heterocyclic carboxylic acid hydrazide for a period of from 1 to 24 hours (h) at a temperature of from room temperature to 60° C. During the reaction or upon cooling, the product generally precipitates from solution and is isolated by filtration. In instances where the product does not readily solidify, the addition of a small amount of water generally initiates precipitation.

Example 1

Preparation of 5-methylthiophene-3-carboxylic acid [1-(2-hydroxyphenyl)-methylidene]-hydrazide (Compound 24)

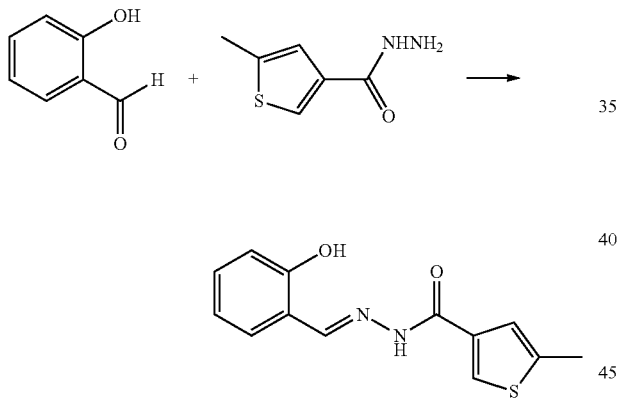

Salicylaldehyde (200 milligrams (mg), 1.62 millimoles (mmol)) and 5-methylthiophene-3-carboxylic acid hydrazide (254 mg, 1.62 mmol) were stirred together in EtOH (5 milliliters (mL)) at room temperature for 3 h. The resulting solid was isolated by filtration to yield the desired material (150 mg, 36%) as a white solid: mp 180-182° C.; $^1$H NMR (400 MHz, DMSO-$d_6$) δ 11.86 (s, 1H), 11.22 (s, 1H), 8.59 (s, 1H), 8.06 (s, 1H), 7.54 (d, J=7.6 Hz, 1H), 7.33-7.25 (m, 2H), 6.97-6.87 (m, 2H), 2.48 (s, 3H); ESIMS m/z 261 ([M+H]$^+$).

General Method B

Preparation of 2-hydroxyphenylaldehyde and 2-hydroxyphenylketone heterocycloylhydrazones from 2-hydroxyphenylaldehydes or 2-hydroxyphenylketones, a heterocyclic carboxylic acid ester, and hydrazine A heterocyclic carboxylic acid ester and hydrazine (3 to 20 molar equivalents) are agitated together in EtOH at 60 to 90° C. for a period of from 1 to 72 h. The crude reaction mixture is cooled to room temperature and evaporated to remove solvent and excess hydrazine. The residue and a 2-hydroxyphenylaldehyde or 2-hydroxyphenylketone (1 molar equivalent) are taken up in a suitable solvent, such as EtOH with or without the addition of up to 10% HOAc, and agitated for a period of from 1 to 24 h at a temperature of from room temperature to 60° C. During the reaction or upon cooling, the product generally precipitates from solution and is isolated by filtration. In instances where the product does not readily solidify, the addition of a small amount of water generally initiates precipitation.

Example 2

Preparation of 1-methyl-piperidine-2-carboxylic acid [1-(3,5-dichloro-2-hydroxy-phenyl)-methylidene]-hydrazide (Compound 54)

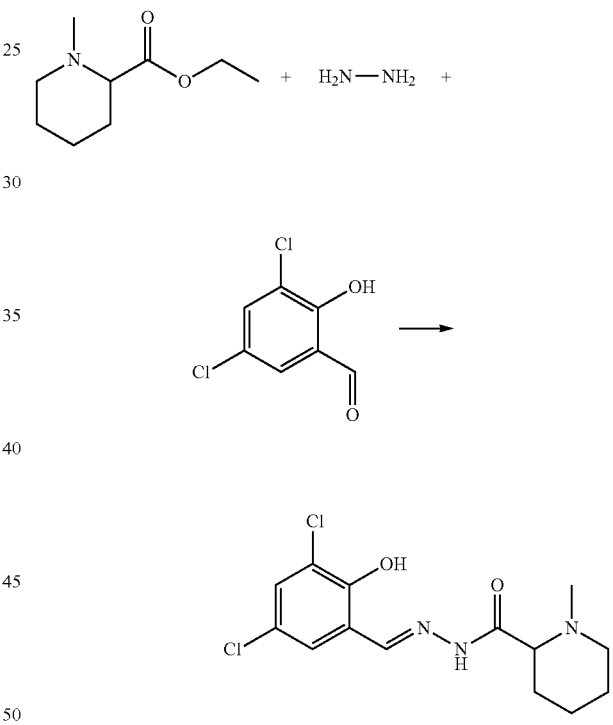

Ethyl 1-methylpiperidine-2-carboxylate (100 mg, 0.584 mmol) and hydrazine (0.108 mL, 3.44 mmol) were added to EtOH (2 mL) and shaken together at 90° C. for 48 h. The reaction mixture was cooled to room temperature. The solvent and excess hydrazine were removed in vacuo.

To the residue were added EtOH (2 mL) and 3,5-dichloro-2-hydroxybenzaldehyde (112 mg, 0.584 mmol). The mixture was shaken and heated to 60° C. for 16 h. Upon cooling the resulting solid was isolated by filtration to yield the desired material (146 mg, 76%) as a pale yellow solid: mp 107-110° C.; $^1$H NMR (400 MHz, DMSO-$d_6$) δ 12.02 (s, 2H), 8.47 (s, 1H), 7.60 (d, J=2.5 Hz, 1H), 7.58 (d, J=2.6 Hz, 1H), 2.95-2.86 (m, 1H), 2.64-2.56 (m, 1H), 2.15 (s, 3H), 2.09-1.96 (m, 1H), 1.81-1.68 (m, 2H), 1.66-1.49 (m, 3H), 1.31-1.17 (m, 1H); ESIMS m/z 330 ([M+H]$^+$), 328 ([M+H]$^-$).

TABLE 1
Structures for Exemplified Compounds
| Compound Number | Structure |
|---|---|
| 1 | 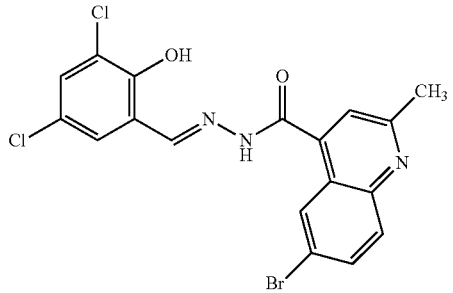 [SMILES: Cc1cc(C(=O)N/N=C/c2cc(Cl)cc(Cl)c2O)c2cc(Br)ccc2n1] |
| 2 | 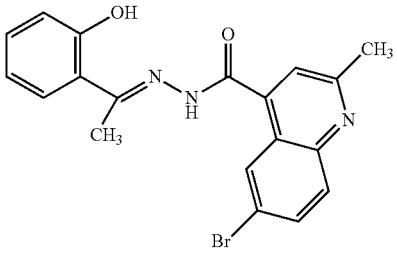 [SMILES: C/C(=N\NC(=O)c1cc(C)nc2ccc(Br)cc12)c1ccccc1O] |
| 3 | 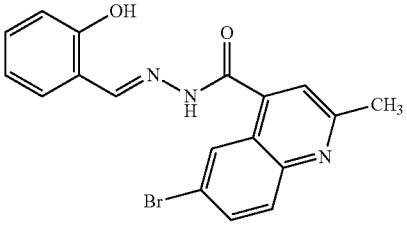 [SMILES: Cc1cc(C(=O)N/N=C/c2ccccc2O)c2cc(Br)ccc2n1] |
| 4 | 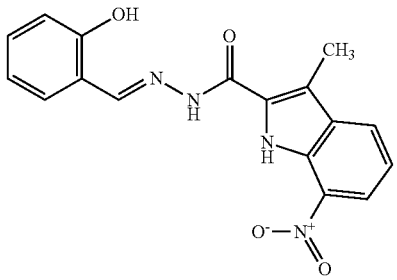 [SMILES: Cc1c(C(=O)N/N=C/c2ccccc2O)[nH]c2c([N+](=O)[O-])cccc12] |
| 5 | 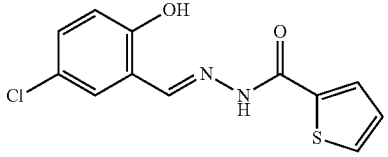 [SMILES: O=C(N/N=C/c1cc(Cl)ccc1O)c1cccs1] |
| 6 | 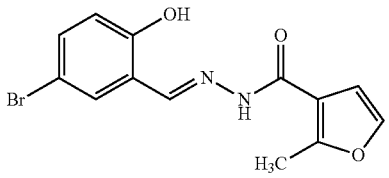 [SMILES: Cc1occc1C(=O)N/N=C/c1cc(Br)ccc1O] |

TABLE 1-continued
Structures for Exemplified Compounds
| Compound Number | Structure |
|---|---|
| 7 | 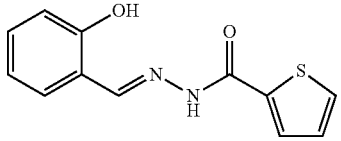 [SMILES: O=C(N/N=C/c1ccccc1O)c1cccs1] |
| 8 | 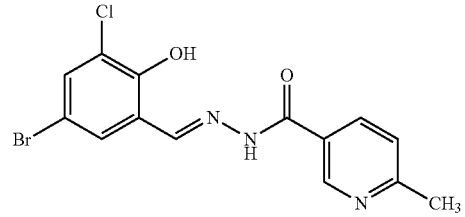 [SMILES: Cc1ccc(C(=O)N/N=C/c2cc(Br)cc(Cl)c2O)cn1] |
| 9 | 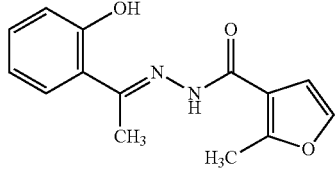 [SMILES: C/C(=N\NC(=O)c1ccoc1C)c1ccccc1O] |
| 10 | 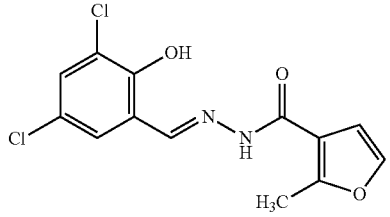 [SMILES: Cc1occc1C(=O)N/N=C/c1cc(Cl)cc(Cl)c1O] |
| 11 | 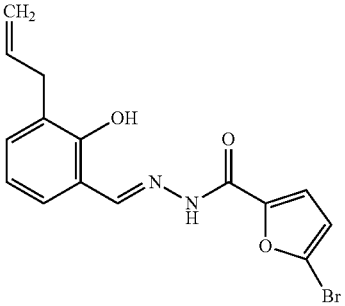 [SMILES: C=CCc1cccc(/C=N/NC(=O)c2ccc(Br)o2)c1O] |
| 12 | 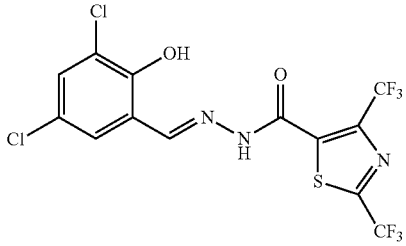 [SMILES: O=C(N/N=C/c1cc(Cl)cc(Cl)c1O)c1sc(C(F)(F)F)nc1C(F)(F)F] |
| 13 | 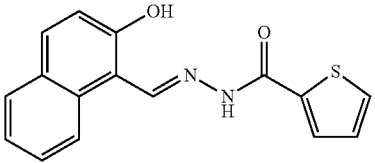 [SMILES: O=C(N/N=C/c1c(O)ccc2ccccc12)c1cccs1] |

TABLE 1-continued

Structures for Exemplified Compounds

| Compound Number | Structure |
|---|---|
| 14 | 3,5-dichloro-2-hydroxybenzaldehyde furan-2-carbohydrazone |
| 15 | 3,5-dichloro-2-hydroxybenzaldehyde 1-methyl-1H-indole-3-carbohydrazone |
| 16 | 3,5-dichloro-2-hydroxybenzaldehyde 1-ethyl-3-methyl-1H-pyrazole-5-carbohydrazone |
| 17 | 3,5-dichloro-2-hydroxybenzaldehyde 1-(4-chlorophenyl)-5-(trifluoromethyl)-1H-pyrazole-4-carbohydrazone |
| 18 | benzaldehyde 1-(4-chlorophenyl)-5-(trifluoromethyl)-1H-pyrazole-4-carbohydrazone |
| 19 | 2-hydroxybenzaldehyde 3-chlorobenzo[b]thiophene-2-carbohydrazone |

TABLE 1-continued

Structures for Exemplified Compounds

| Compound Number | Structure |
|---|---|
| 20 | *(2-hydroxybenzylidene hydrazide of benzo[b]thiophene-2-carboxylic acid)* |
| 21 | *(2-hydroxybenzylidene hydrazide of 5-methyl-2-phenyl-2H-1,2,3-triazole-4-carboxylic acid)* |
| 22 | *(2-hydroxybenzylidene hydrazide of 4-phenyl-1,2,3-thiadiazole-5-carboxylic acid)* |
| 23 | *(2-hydroxybenzylidene hydrazide of 5-chlorothiophene-2-carboxylic acid)* |
| 24 | *(2-hydroxybenzylidene hydrazide of 5-methylthiophene-3-carboxylic acid)* |
| 25 | *(3,5-dichloro-2-hydroxybenzylidene hydrazide of 2,4-dimethylthiazole-5-carboxylic acid)* |

TABLE 1-continued
Structures for Exemplified Compounds
| Compound Number | Structure |
|---|---|
| 26 | 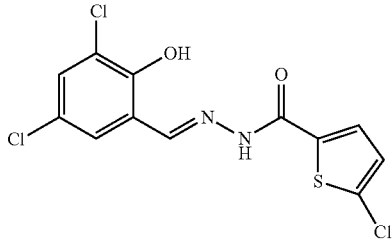 [SMILES: O=C(N/N=C/c1cc(Cl)cc(Cl)c1O)c1ccc(Cl)s1] |
| 27 | 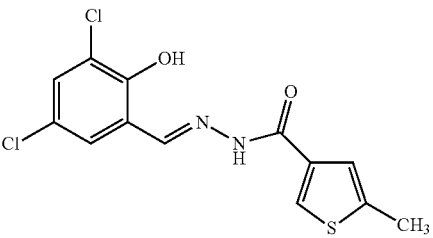 [SMILES: Cc1cc(C(=O)N/N=C/c2cc(Cl)cc(Cl)c2O)cs1] |
| 28 | 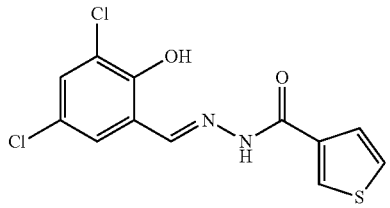 [SMILES: O=C(N/N=C/c1cc(Cl)cc(Cl)c1O)c1ccsc1] |
| 29 | 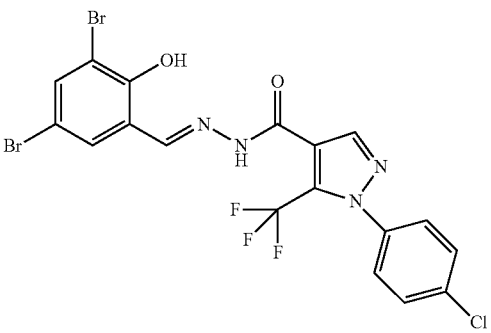 [SMILES: O=C(N/N=C/c1cc(Br)cc(Br)c1O)c1cnn(-c2ccc(Cl)cc2)c1C(F)(F)F] |
| 30 | 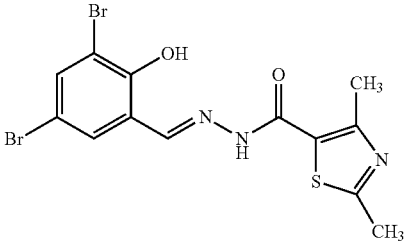 |
| 31 | 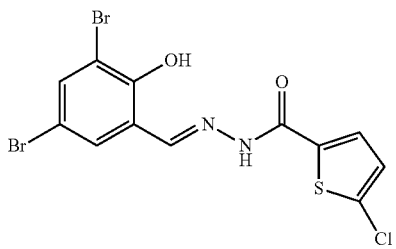 [SMILES: O=C(N/N=C/c1cc(Br)cc(Br)c1O)c1ccc(Cl)s1] |

TABLE 1-continued
Structures for Exemplified Compounds
| Compound Number | Structure |
|---|---|
| 32 | 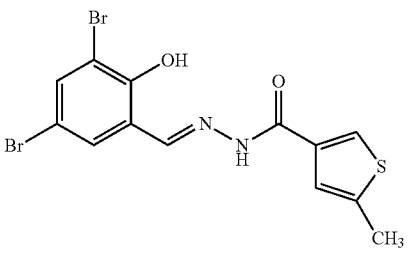 [SMILES: Cc1cc(C(=O)N/N=C/c2cc(Br)cc(Br)c2O)cs1] |
| 33 | 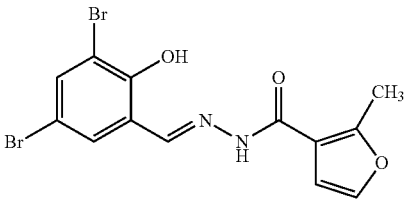 [SMILES: Cc1occc1C(=O)N/N=C/c1cc(Br)cc(Br)c1O] |
| 34 | 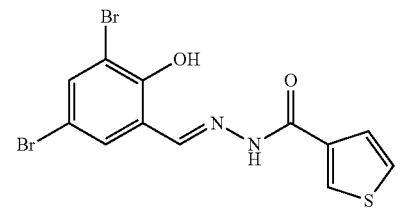 |
| 35 | 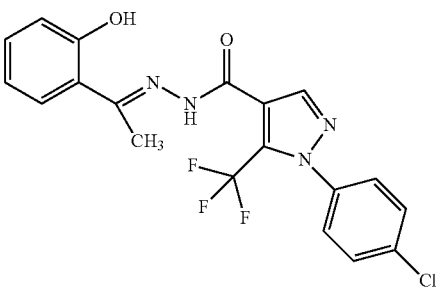 [SMILES: C/C(=N\NC(=O)c1cnn(-c2ccc(Cl)cc2)c1C(F)(F)F)c1ccccc1O] |
| 36 | 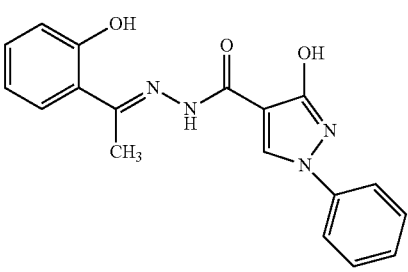 [SMILES: C/C(=N\NC(=O)c1cn(-c2ccccc2)nc1O)c1ccccc1O] |
| 37 | 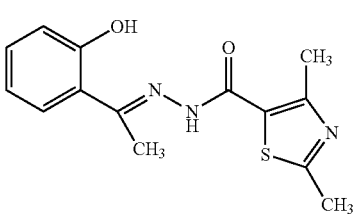 [SMILES: C/C(=N\NC(=O)c1sc(C)nc1C)c1ccccc1O] |

TABLE 1-continued

Structures for Exemplified Compounds

| Compound Number | Structure |
|---|---|
| 38 | 2-hydroxyphenyl-C(CH₃)=N-NH-C(O)-(5-chlorothiophen-2-yl) |
| 39 | 2-hydroxyphenyl-C(CH₃)=N-NH-C(O)-(5-methylthiophen-3-yl) |
| 40 | 2-hydroxyphenyl-C(CH₃)=N-NH-C(O)-(thiophen-3-yl) |
| 41 | 3,5-dichloro-2-hydroxyphenyl-C(CH₃)=N-NH-C(O)-[5-(trifluoromethyl)-1-(4-chlorophenyl)-1H-pyrazol-4-yl] |
| 42 | 3,5-dichloro-2-hydroxyphenyl-C(CH₃)=N-NH-C(O)-(3-hydroxy-1-phenyl-1H-pyrazol-4-yl) |
| 43 | 3,5-dichloro-2-hydroxyphenyl-C(CH₃)=N-NH-C(O)-(2,4-dimethylthiazol-5-yl) |

TABLE 1-continued

Structures for Exemplified Compounds

| Compound Number | Structure |
|---|---|
| 44 | 3,5-dichloro-2-hydroxyphenyl methyl ketone N-acylhydrazone with 5-chlorothiophene-2-carboxylic acid |
| 45 | 3,5-dichloro-2-hydroxyphenyl methyl ketone N-acylhydrazone with 5-methylthiophene-3-carboxylic acid |
| 46 | 3,5-dichloro-2-hydroxyphenyl methyl ketone N-acylhydrazone with 2-methylfuran-3-carboxylic acid |
| 47 | 3,5-dichloro-2-hydroxyphenyl methyl ketone N-acylhydrazone with thiophene-3-carboxylic acid |
| 48 | 3,5-dibromo-2-hydroxyphenyl methyl ketone N-acylhydrazone with 1-(4-chlorophenyl)-5-(trifluoromethyl)-1H-pyrazole-4-carboxylic acid |
| 49 | 3,5-dibromo-2-hydroxyphenyl methyl ketone N-acylhydrazone with 2,4-dimethylthiazole-5-carboxylic acid |

TABLE 1-continued

Structures for Exemplified Compounds

| Compound Number | Structure |
|---|---|
| 50 | 1-(3,5-dibromo-2-hydroxyphenyl)ethylidene hydrazide of 5-chlorothiophene-2-carboxylic acid |
| 51 | 1-(3,5-dibromo-2-hydroxyphenyl)ethylidene hydrazide of 5-methylthiophene-3-carboxylic acid |
| 52 | 1-(3,5-dibromo-2-hydroxyphenyl)ethylidene hydrazide of 2-methylfuran-3-carboxylic acid |
| 53 | 1-(3,5-dibromo-2-hydroxyphenyl)ethylidene hydrazide of thiophene-3-carboxylic acid |
| 54 | (3,5-dichloro-2-hydroxybenzylidene) hydrazide of 1-methylpiperidine-2-carboxylic acid |

TABLE 2

Analytical Data for Compounds in Table 1

| Compound Number | Synthesis Method | Appearance | mp (° C.) | ESIMS (+) | ESIMS (−) | $^1$H NMR (400 MHz, DMSO-$d_6$ unless otherwise stated), δ |
|---|---|---|---|---|---|---|
| 1 | A | yellow solid | 265-267 | 454 | 452 | 12.84 (s, 1H), 12.23 (s, 1H), 8.53 (s, 1H), 8.38 (d, J = 2.0 Hz, 1H), 8.00-7.92 (m, 2H), 7.78 (s, 1H), 7.75 (d, J = 2.5 Hz, 1H), 7.69 (d, J = 2.5 Hz, 1H), 2.73 (s, 3H) |

TABLE 2-continued

Analytical Data for Compounds in Table 1

| Compound Number | Synthesis Method | Appearance | mp (° C.) | ESIMS (+) | ESIMS (−) | $^1$H NMR (400 MHz, DMSO-$d_6$ unless otherwise stated), δ |
|---|---|---|---|---|---|---|
| 2 | A | off-white solid | 251-254 | 399 | 397 | 13.24 (s, 1H), 11.82 (s, 1H), 8.35-8.27 (m, 1H), 8.02-7.85 (m, 2H), 7.79 (s, 1H), 7.67 (dd, J = 8.0, 1.5 Hz, 1H), 7.38-7.31 (m, 1H), 6.98-6.90 (m, 2H), 2.76-2.68 (m, 3H), 2.48-2.41 (m, 3H) |
| 3 | A | off-white solid | 270-275 | 384 | 382 | 12.41 (s, 1H), 11.00 (s, 1H), 8.59 (s, 1H), 8.38 (d, J = 2.0 Hz, 1H), 7.99-7.90 (m, 2H), 7.76 (s, 1H), 7.64 (dd, J = 7.7, 1.6 Hz, 1H), 7.37-7.31 (m, 1H), 6.99-6.92 (m, 2H), 2.74-2.69 (m, 3H) |
| 4 | A | yellow solid | 296-299 | 339 | 337 | 12.37 (s, 1H), 11.65 (s, 1H), 11.24 (s, 1H), 8.63 (s, 1H), 8.30 (d, J = 7.8 Hz, 1H), 8.24 (d, J = 7.7 Hz, 1H), 7.62 (d, J = 7.3 Hz, 1H), 7.38-7.29 (m, 2H), 6.98-6.91 (m, 2H), 2.64 (s, 3H) |
| 5 | A | off-white solid | | 281 | 279 | |
| 6 | A | off-white solid | | 323 | 321 | |
| 7 | A | off-white solid | | 247 | 245 | |
| 8 | A | yellow solid | | 369 | 367 | |
| 9 | A | white solid | | 259 | 257 | |
| 10 | A | yellow solid | | 313 | 311 | |
| 11 | A | yellow solid | | 350 | 348 | |
| 12 | A | yellow solid | 189-190 | 452 | 450 | Appears as two isomers in DMSO: 13.00 (s, 1H), 12.80 (s, 1H), 11.81 (s, 1H), 10.40 (s, 1H), 8.50 (s, 1H), 8.43 (s, 1H), 7.74 (d, J = 2.5 Hz, 1H), 7.69 (d, J = 2.5 Hz, 1H), 7.64 (d, J = 2.6 Hz, 1H), 7.48 (d, J = 2.6 Hz, 1H) |
| 13 | A | orange solid | | 297 | 295 | |
| 14 | A | pale yellow solid | | 299 | 297 | |
| 15 | A | pale yellow solid | 215-217 | 362 | 360 | 12.59 (s, 1H), 12.50 (s, 1H), 8.57 (s, 1H), 7.73 (d, J = 8.0 Hz, 1H), 7.70 (d, J = 2.5 Hz, 1H), 7.64 (d, J = 2.5 Hz, 1H), 7.61 (d, J = 8.2 Hz, 1H), 7.39-7.31 (m, 2H), 7.19-7.12 (m, 1H), 4.05 (s, 3H) |
| 16 | A | white solid | 221-222 | 341 | 339 | 12.41 (s, 1H), 12.31 (s, 1H), 8.53 (s, 1H), 7.69 (d, J = 2.5 Hz, 1H), 7.65 (d, J = 2.5 Hz, 1H), 6.79 (s, 1H), 4.45 (q, J = 7.1 Hz, 2H), 2.22 (s, 3H), 1.32 (t, J = 7.1 Hz, 3H) |
| 17 | A | white solid | 216-217 | 477 | 475 | 12.64 (s, 1H), 12.17 (s, 1H), 8.51 (s, 1H), 8.35 (s, 1H), 7.73-7.60 (m, 6H) |
| 18 | A | white solid | 205-207 | 409 | 407 | Appears as two isomers in DMSO: 12.26-11.98 (m, 1H), 11.02-10.00 (m, 1H), 8.62-8.37 (m, 1H), 8.36-8.18 (m, 1H), 7.73-7.66 (m, 2H), 7.66-7.49 (m, 3H), 7.36-7.20 (m, 1H), 6.98-6.82 (m, 2H) |
| 19 | A | pale yellow solid | | 331 | 329 | |

TABLE 2-continued

Analytical Data for Compounds in Table 1

| Compound Number | Synthesis Method | Appearance | mp (° C.) | ESIMS (+) | ESIMS (−) | $^1$H NMR (400 MHz, DMSO-$d_6$ unless otherwise stated), δ |
|---|---|---|---|---|---|---|
| 20 | A | pale yellow solid | 220-221 | 297 | 295 | Appears as two isomers in DMSO: 12.46-11.91 (m, 1H), 11.11-10.07 (m, 1H), 8.74-8.46 (m, 1H), 8.45-8.20 (m, 1H), 8.10-7.58 (m, 3H), 7.55-7.43 (m, 2H), 7.36-7.25 (m, 1H), 7.00-6.90 (m, 2H) |
| 21 | A | white solid | 231-233 | 322 | 320 | 12.28 (s, 1H), 11.18 (s, 1H), 8.77 (s, 1H), 8.15-8.04 (m, 2H), 7.66-7.60 (m, 2H), 7.56 (dd, J = 7.6, 1.5 Hz, 1H), 7.53-7.47 (m, 1H), 7.36-7.29 (m, 1H), 6.97-6.91 (m, 2H), 2.60 (s, 3H) |
| 22 | A | yellow solid | 191-192 | 325 | 323 | Appears as two isomers in DMSO: 12.57-12.25 (m, 1H), 10.87-10.03 (m, 1H), 8.55-8.38 (m, 1H), 7.93-7.60 (m, 3H), 7.60-7.48 (m, 3H), 7.35-7.23 (m, 1H), 6.96-6.87 (m, 2H) |
| 23 | A | pale yellow solid | 228-230 | 281 | | |
| 24 | A | white solid | 180-182 | 261 | | 11.86 (s, 1H), 11.22 (s, 1H), 8.59 (s, 1H), 8.06 (s, 1H), 7.54 (d, J = 7.6 Hz, 1H), 7.33-7.25 (m, 2H), 6.97-6.87 (m, 2H), 2.48 (s, 3H) |
| 25 | A | pale yellow solid | 217-219 | 344 | | 12.35 (s, 1H), 11.93 (s, 1H), 8.52 (s, 1H), 7.66 (s, 1H), 7.63 (s, 1H), 2.68 (s, 3H), 2.60 (s, 3H) |
| 26 | A | white solid | 248-250 | | 347 | 12.58 (s, 1H), 12.17 (s, 1H), 8.54 (s, 1H), 7.85-7.80 (m, 1H), 7.70 (s, 1H), 7.66-7.62 (m, 1H), 7.34-7.27 (m, 1H) |
| 27 | A | pale yellow solid | 189-191 | 329 | | 12.47 (s, 1H), 12.28 (s, 1H), 8.52 (s, 1H), 8.11 (s, 1H), 7.67 (d, J = 2.1 Hz, 1H), 7.62 (d, J = 2.3 Hz, 1H), 7.31 (s, 1H)* |
| 28 | A | white solid | 315-318 | 315 | | 12.47 (s, 1H), 12.36 (s, 1H), 8.54 (s, 1H), 8.39-8.34 (m, 1H), 7.73-7.66 (m, 2H), 7.64-7.60 (m, 2H) |
| 29 | A | white solid | 237-238 | 567 | | 12.67 (s, 1H), 12.41 (s, 1H), 8.47 (s, 1H), 8.35 (s, 1H), 7.86 (s, 2H), 7.70 (d, J = 8.7 Hz, 2H), 7.62 (d, J = 8.7 Hz, 2H) |
| 30 | A | pale yellow solid | 225-226 | 434 | | |
| 31 | A | white solid | 247-248 | | 437 | 12.62 (s, 1H), 12.41 (s, 1H), 8.50 (s, 1H), 7.87-7.81 (m, 3H), 7.31 (d, J = 3.9 Hz, 1H) |
| 32 | A | white solid | 203-205 | 419 | | 12.69 (s, 1H), 12.31 (s, 1H), 8.48 (s, 1H), 8.11 (s, 1H), 7.85-7.79 (m, 2H), 7.31 (s, 1H)* |
| 33 | A | yellow solid | 270-272 | 403 | | |
| 34 | A | off-white solid | 236-237 | 405 | | 12.68 (s, 1H), 12.39 (s, 1H), 8.50 (s, 1H), 8.36 (s, 1H), 7.86-7.79 (m, 2H), 7.74-7.68 (m, 1H), 7.62 (d, J = 4.9 Hz, 1H) |
| 35 | A | light brown solid | 201-202 | 423 | | 13.10 (s, 1H), 11.60 (s, 1H), 8.37 (s, 1H), 7.70 (d, J = 8.4 Hz, 2H), 7.67-7.57 (m, 3H), 7.32 (t, J = 7.6 Hz, 1H), 6.97-6.88 (m, 2H), 2.46 (s, 3H). |

TABLE 2-continued

Analytical Data for Compounds in Table 1

| Compound Number | Synthesis Method | Appearance | mp (° C.) | ESIMS (+) | ESIMS (−) | $^1$H NMR (400 MHz, DMSO-$d_6$ unless otherwise stated), δ |
|---|---|---|---|---|---|---|
| 36 | A | light brown solid | 276-277 | 337 | | 13.10 (s, 1H), 10.80 (s, 1H), 10.38 (s, 1H), 8.16 (s, 1H), 7.91 (s, 1H), 7.89 (s, 1H), 7.66 (d, J = 7.9 Hz, 1H), 7.56-7.50 (m, 2H), 7.36 (t, J = 7.4 Hz, 1H), 7.32 (t, J = 8.0 Hz, 1H), 6.95-6.88 (m, 2H), 2.45 (s, 3H) |
| 37 | A | yellow solid | 202-204 | 290 | | 13.15 (s, 1H), 11.16 (s, 1H), 7.61 (s, 1H), 7.30 (t, J = 7.6 Hz, 1H), 6.94-6.87 (m, 2H), 2.67 (s, 3H), 2.58 (s, 3H), 2.42 (s, 3H) |
| 38 | A | white solid | 204-205 | 295 | | 13.07 (s, 1H), 11.36 (s, 1H), 7.95 (s, 1H), 7.63 (s, 1H), 7.36-7.25 (m, 2H), 6.95-6.86 (m, 2H)* |
| 39 | A | off-white solid | 158-160 | 275 | | 13.29 (s, 1H), 11.03 (s, 1H), 8.15 (s, 1H), 7.63 (d, J = 7.5 Hz, 1H), 7.34-7.26 (m, 2H), 6.94-6.86 (m, 2H), 2.47 (s, 3H)* |
| 40 | A | pale brown solid | 148-150 | 261 | | 13.29 (s, 1H), 11.12 (s, 1H), 8.41 (s, 1H), 7.69 (dd, J = 5.0, 2.9 Hz, 1H), 7.66-7.60 (m, 2H), 7.30 (t, J = 7.1 Hz, 1H), 6.94-6.87 (m, 2H), 2.48 (s, 3H) |
| 41 | A | pale yellow solid | 209-211 | 491 | | (400 MHz, CD$_3$OD) 8.18 (s, 1H), 7.63-7.58 (m, 3H), 7.55-7.50 (m, 2H), 7.46 (s, 1H), 2.47 (s, 3H) |
| 42 | A | pale brown solid | 269-271 | 405 | | 14.22 (s, 1H), 11.00 (s, 1H), 10.37 (s, 1H), 8.17 (s, 1H), 7.93-7.88 (m, 2H), 7.71 (s, 1H), 7.64 (s, 1H), 7.57-7.50 (m, 2H), 7.40-7.34 (m, 1H), 2.47 (s, 3H) |
| 43 | A | yellow solid | 208-209 | 358 | | 14.27 (s, 1H), 11.44 (s, 1H), 7.69-7.65 (m, 1H), 7.64 (d, J = 2.0 Hz, 1H), 2.68 (s, 3H), 2.58 (s, 3H), 2.45 (s, 3H) |
| 44 | A | yellow solid | 221-224 | 363 | | 14.15 (s, 1H), 11.58 (s, 1H), 7.99 (s, 1H), 7.67 (s, 1H), 7.64 (s, 1H), 7.32 (d, J = 3.6 Hz, 1H)* |
| 45 | A | off-white solid | 218-220 | 343 | | (400 MHz, DMSO + D$_2$O) 8.18 (s, 1H), 7.67 (d, J = 2.2 Hz, 1H), 7.63 (d, J = 2.2 Hz, 1H), 7.33 (s, 1H), 2.50 (s, 3H), 2.49 (s, 3H) |
| 46 | A | yellow solid | 212-215 | 327 | | |
| 47 | A | yellow solid | 230-232 | 329 | | 8.36 (s, 1H), 7.86 (s, 1H), 7.82 (s, 1H), 7.71 (d, J = 8.2 Hz, 2H), 7.61 (d, J = 8.3 Hz, 2H), 2.47 (s, 3H) |
| 48 | A | pale yellow solid | 121-125 | 581 | | (400 MHz, DMSO + D$_2$O) 8.36 (s, 1H), 7.86 (s, 1H), 7.82 (s, 1H), 7.71 (d, J = 8.2 Hz, 2H), 7.61 (d, J = 8.3 Hz, 2H), 2.47 (s, 3H) |
| 49 | A | pale yellow solid | 221-223 | 448 | | 14.40 (s, 1H), 11.45 (s, 1H), 7.85-7.83 (m, 1H), 7.81-7.79 (m, 1H), 2.68 (s, 3H), 2.58 (s, 3H), 2.45 (s, 3H) |
| 50 | A | white solid | 253-255 | | 451 | 14.29 (s, 1H), 11.59 (s, 1H), 7.99 (s, 1H), 7.84 (s, 1H), 7.81 (s, 1H), 7.32 (d, J = 3.9 Hz, 1H)* |

TABLE 2-continued

Analytical Data for Compounds in Table 1

| Compound Number | Synthesis Method | Appearance | mp (° C.) | ESIMS (+) | ESIMS (−) | $^1$H NMR (400 MHz, DMSO-$d_6$ unless otherwise stated), δ |
|---|---|---|---|---|---|---|
| 51 | A | white solid | 237-239 | 433 | | (400 MHz, CDCl$_3$) 13.46 (s, 1H), 8.76 (s, 1H), 7.77 (s, 1H), 7.68 (d, J = 2.1 Hz, 1H), 7.52 (d, J = 2.2 Hz, 1H), 7.12 (s, 1H), 2.53 (s, 3H), 2.36 (s, 3H) |
| 52 | A | white solid | 201-204 | 417 | | 14.58 (s, 1H), 11.08 (s, 1H), 7.85-7.81 (m, 1H), 7.81-7.78 (m, 1H), 7.66-7.63 (m, 1H), 7.04 (s, 1H), 2.58 (s, 3H), 2.48 (s, 3H) |
| 53 | A | pale yellow solid | 251-253 | 419 | | 14.53 (s, 1H), 11.36 (s, 1H), 8.46 (s, 1H), 7.85-7.82 (m, 1H), 7.82-7.79 (m, 1H), 7.72-7.68 (m, 1H), 7.63 (d, J = 4.9 Hz, 1H)* |
| 54 | B | pale yellow solid | 107-110 | 330 | 328 | 12.02 (s, 2H), 8.47 (s, 1H), 7.60 (d, J = 2.5 Hz, 1H), 7.58 (d, J = 2.6 Hz, 1H), 2.95-2.86 (m, 1H), 2.64-2.56 (m, 1H), 2.15 (s, 3H), 2.09-1.96 (m, 1H), 1.81-1.68 (m, 2H), 1.66-1.49 (m, 3H), 1.31-1.17 (m, 1H) |

*Methyl resonance was obscured by the solvent resonance.

Example 3

Effect of Copper on Fungitoxicity of Hydrazones Towards *Leptosphaeria nodorum*

In vitro fungitoxicity assays against *Leptosphaeria nodorum* (LEPTNO) were conducted using the liquid growth medium described by Coursen and Sisler (*American Journal of Botany* 1960, 47, 541-549) except that copper micronutrient, normally included as $CuSO_4$, was omitted. The medium, termed “copper-minus”, was prepared by dissolving 10 g glucose, 1.5 g $K_2HPO_4$, 2 g $KH_2PO_4$ and 1 g $(NH_4)_2SO_4$ in 1 liter of deionized water and treating the solution with 0.5 g Chelex 100 resin (Bio-Rad Analytical grade, 50-100 mesh, sodium form, cat#142-2822) by stirring at room temperature for 1 h. $MgSO_4.7H_2O$ (0.5 g) was added, and stirring was continued for a further hour. Trace elements (minus $CuSO_4$), and vitamins described by Coursen and Sisler were added from concentrated stock solutions and the entire medium was sterilized by filtration. Medium containing copper was prepared by adding $CuCl_2.2H_2O$ to the copper-minus medium at 20 μM. Test compounds were dissolved in dimethylsulfoxide (DMSO) at 10 ng/mL and 1 μl, aliquots were added to two wells of flat-bottomed 96-well microtiter plates. Copper-minus medium (100 μL) was added to one of the wells and copper-plus medium to the second well. Control wells, included for each medium, received 1 μL DMSO and 100 μL of medium.

LEPTNO was grown on potato dextrose agar in 9 cm diameter petri dishes for 7 days (d). Sterile deionized water (20 mL) was added to a culture plate and spores suspended by scraping the surface gently with a sterile plastic loop. The resulting suspension was filtered through a double layer of sterile cheesecloth. Filtered spore suspension (5 mL) was centrifuged in a bench centrifuge at 2000 rpm for 2 min The resulting spore pellet was resuspended in 10 mL sterile deionized water (which had been treated with Chelex 100 resin using 0.5 g resin per liter of water by stirring at room temperature for 1 h), and recentrifuged. The spores were resuspended in copper-minus medium, and the suspension adjusted to $2\times10^5$ spores per mL. Microtiter plates were inoculated with 100 μL of this spore suspension and the plates incubated at 25° C. for 72 h before assessing fungal growth by measuring light scattering in a NepheloStar plate reader. Growth inhibition was determined by comparing growth in the presence of test compound with growth in control wells lacking test compound.

Results for growth inhibition by test compounds at 0.05 μg/mL in copper-plus medium (% Inhn Plus Copper Observed) were compared with predicted values (% Inhn Plus Copper Predicted) that were calculated using the formula set forth by S. R. Colby in *Weeds* 1967, 15, 20-22 based on results obtained for the same compounds in copper-minus medium (% Inhn Minus Copper Observed) and the inhibition attributed to copper chloride alone, as determined by comparing growth in copper-minus and copper-plus media without any test compound across experiments. Data are presented in Table 3. Results illustrate that hydrazones and copper produce a synergistic fungitoxic effect towards LEPTNO.

Example 4

Efficacy of Hydrazones in Mixture with Copper Against Tomato Blight (*Phytophthora infestans*)

Hydrazone compounds at 50 ppm in combination with 50 μM $CuCl_2.2H_2O$ were evaluated as prophylactic treatments applied 24 h before inoculation. Efficacy was determined based on percentage of disease control against tomato late blight (TLB), causal agent *Phytophthora infestans*. Treatments were arranged in a completely randomized design with 3 repetitions each. A pot with one tomato plant was considered as an experimental unit. Hydrazones were dissolved in acetone and re-suspended in water containing 0.01% Triton® X-100, 0.1% Atlox 4913 and 50 μM $CuCl_2.2H_2O$ to a final concentration of 10% acetone. All treatments were applied to run off 24 h before inoculation using a spin-table sprayer. Inoculation with an aqueous suspension of *P. infestans* sporangia was performed using a Delta painting sprayer. Percentage of disease control was determined 7 d after inoculation. Data are presented in Table 3, and illustrate the efficacy of hydrazones in mixture with copper for control of tomato late blight.

TABLE 3

Biological Data for Compounds in Table 1

| Compound Number | LEPTNO % Inhn. Minus Copper Observed | LEPTNO % Inhn. Plus Copper Observed | LEPTNO % Inhn. Plus Copper Predicted | TLB % control |
|---|---|---|---|---|
| 1 | 2.5 | 73.8 | 11.6 | 7 |
| 2 | 0 | 83.4 | 9.3 | 36 |
| 3 | 0 | 72.9 | 9.3 | 25 |
| 4 | 11.3 | 91.4 | 19.6 | 4 |
| 5 | 0 | 95.8 | 9.3 | 54 |
| 6 | 2.2 | 96.7 | 11.3 | 75 |
| 7 | 0 | 87.3 | 9.3 | 38 |
| 8 | 0 | 60.9 | 9.3 | 0 |
| 9 | 3.9 | 97 | 12.8 | 60 |
| 10 | 8.7 | 98.1 | 17.2 | 67 |
| 11 | 12.9 | 95.1 | 21 | 31 |
| 12 | 49.8 | 94.7 | 54.4 | 57 |
| 13 | 0.9 | 86.4 | 10.1 | 62 |
| 14 | 0 | 56.2 | 9.3 | 52 |
| 15 | 16.3 | 98.1 | 24 | 12 |
| 16 | 3.5 | 88 | 12.5 | 39 |
| 17 | 15.8 | 92.6 | 23.6 | 69 |
| 18 | 0 | 92.5 | 9.3 | 7 |
| 19 | 0 | 92.1 | 9.3 | 44 |
| 20 | 4.2 | 95.4 | 13.1 | 18 |
| 21 | 0 | 93.9 | 9.3 | 16 |
| 22 | 9.6 | 77.9 | 18 | 56 |
| 23 | 0 | 96.3 | 9.3 | 32 |
| 24 | 2.9 | 94.8 | 11.9 | 56 |
| 25 | 0 | 81.9 | 9.3 | 71 |
| 26 | 2.7 | 97.5 | 11.7 | 92 |
| 27 | 5.4 | 97.3 | 14.2 | 78 |
| 28 | 4.4 | 97.6 | 13.3 | 80 |
| 29 | 7.8 | 57.6 | 16.4 | 47 |
| 30 | 1 | 71.2 | 10.2 | 49 |
| 31 | 4.9 | 97.8 | 13.7 | 88 |
| 32 | 0 | 97.6 | 9.3 | 69 |
| 33 | 9.1 | 97.8 | 17.5 | 66 |
| 34 | 0 | 97.9 | 9.3 | 80 |
| 35 | 4.3 | 94.8 | 13.2 | 59 |
| 36 | 9.2 | 92.5 | 17.6 | 66 |
| 37 | 0 | 94.2 | 9.3 | 81 |
| 38 | 0 | 98 | 9.3 | 56 |
| 39 | 0 | 97.3 | 9.3 | 66 |
| 40 | 0 | 96.8 | 9.3 | 80 |
| 41 | 0 | 71.3 | 9.3 | 36 |
| 42 | 3.5 | 91.2 | 12.4 | 2 |
| 43 | 0 | 94.3 | 9.3 | 66 |
| 44 | 2 | 96.9 | 11.1 | 68 |
| 45 | 3.7 | 98.3 | 12.6 | 83 |
| 46 | 0 | 97.2 | 9.3 | 69 |
| 47 | 0 | 98.1 | 9.3 | 81 |
| 48 | 4.3 | 56 | 13.2 | 19 |
| 49 | 2.6 | 89.1 | 11.6 | 61 |
| 50 | 0 | 97.5 | 9.3 | 85 |
| 51 | 2.2 | 98 | 11.3 | 88 |
| 52 | 0 | 97.7 | 9.3 | 66 |
| 53 | 7.6 | 97.6 | 16.2 | 73 |
| 54 | 0 | 91 | 9.3 | 22 |
| $CuCl_2$ 10 μM | 9.3 ± 1.6 | | | |

The invention claimed is:

1. A synergistic mixture for controlling the growth of fungi, the mixture comprising:

a source of copper; and a hydrazone compound of Formula I:

Formula I wherein $R_1$ is H, or $C_1$-$C_6$ alkyl;

$R_2$ is a substituted or unsubstituted 5- or 6-membered heteroaromatic, and a 5- or 6-membered saturated, or partially saturated heterocyclic ring whose members consist of carbon and at least one other atom chosen from O, N, or S which may optionally be fused with a second substituted or unsubstituted 5- or 6-membered aromatic, saturated, or partially saturated ring whose members consist of carbon or whose members consist of carbon and one or more other atoms chosen from O, N, or S;

wherein said $R_2$ is selected from unsubstituted thiophene (thienyl); halogen substituted thiophene; alkyl substituted thiophene; unsubstituted furyl; halogen substituted furyl; alkyl substituted pyridyl; haloalkyl or alkyl substituted 1,3-thiazolyl; N-alkyl indolyl; hydroxyl, alkyl or haloalkyl substituted 1,2-diazoyl; alkyl plus phenyl substituted 1,2,3-triazolyl; phenyl substituted 1,2,3-thiadiazolyl; alkyl substituted piperidinyl; alkyl plus halogen substituted quinolinonyl;

and $X_3$ is H, halogen, or $C_2$-$C_6$ alkenyl;

$X_4$ is H;

$X_5$ is H or halogen;

$X_6$ is H;

with the proviso that $X_5$ and $X_6$ may form a 6-membered aromatic fused ring consisting of carbon and hydrogen;

with the proviso that when said R2 is said unsubstituted thiopene(thienyl) then X5 is halogen or X5 and X6 form the 6-membered aromatic ring whose ring members consist of carbon or X3, X4, X5, X6, R1 are hydrogen or then X3 and X5 are halogen;

with the proviso that when said R2 is said halogen substituted thiophene then X3, X4, X5, and X6 are hydrogen, and R1 is selected from hydrogen and methyl or then X3 and X5 are halogen;

with the proviso that when said R2 is said alkyl substituted thiophene then X3, X4, X5, and X6 are hydrogen, and R1 is selected from hydrogen and methyl or then X3 and X5 are halogen;

with the proviso that when said R2 is said unsubstituted furyl then X5 is halogen;

with the proviso that when said R2 is said alkyl substituted furyl then X5 is halogen or hydrogen;

with the proviso that when said R2 is said halogen substituted furyl then X3 is alkenyl;

with the proviso that when said R2 is said alkyl substituted pyridyl then X3 and X5 are halogen;

with the proviso that when said R2 is said haloalkyl or alkyl substituted 1,3-thiazole then X3 and X5 are halogen;

with the proviso that when said R2 is said alkyl substituted 1,3-thiazole then X3, X4, X5 and X6 are hydrogen and R1 is alkyl;

with the proviso that when said R2 is said N-alkyl indolyl then X5 is halogen;

with the proviso that when said R2 is said hydroxyl, alkyl or haloalkyl substituted 1,2-diazolyl then X3 and X5 are halogen;

with the proviso that when said R2 is said haloalkyl substituted 1,2-diazolyl then X3, X4, X5 and X6 are hydrogen and R1 is hydrogen or alkyl;

with the proviso that when said R2 is said hydroxyl substituted 1,2-diazolyl then X3, X4, X5 and X6 are hydrogen and R1 is alkyl;

with the proviso that when said R2 is said alkyl plus phenyl substituted 1,2,3-triazoyl then X3, X4, X5, X6 and R1 are hydrogen;

with the proviso that when R2 is said phenyl substituted 1,2,3-thiadiazolyl then X3, X4, X5, X6 and R1 are hydrogen;

with the proviso that when R2 is said N-alkyl substituted piperidinyl then X3 and X5 are halogen;

with the proviso that when R2 is said alkyl plus halogen substituted quinolinonyl then X4 and X6 are hydrogen; and wherein the copper and said compound of Formula I are present in synergistically effective amounts to control the growth of fungi.

2. The synergistic mixture of claim 1, wherein a growth inhibiting amount of a compound of Formula 1 in mixture with copper is provided as a mixture in which the total molar ratio of copper to the compound of Formula I is 1:1.

3. The synergistic mixture of claim 1, wherein a growth inhibiting amount of a compound of Formula 1 is provided as an isolated hydrazone-copper complex in which the molar ratio of the copper to the compound of Formula I ranges from 1:1 to 1:2.

4. The synergistic mixture of claim 1, wherein the compound of Formula 1 to be combined with copper is complexed with a metal.

5. The synergistic mixture of claim 4, wherein the metal complexed with the compound of Formula I is selected from the group consisting of $Cu^+$, $Cu^{2+}$, $Fe^{2+}$, $Fe^{3+}$, $Zn^{2+}$, and $Mn^{2+}$.

6. The synergistic mixture of claim 1, wherein the source of copper is selected from the group consisting of: copper oxychloride, copper octanoate, copper ammonium carbonate, copper arsenate, copper oxysulfate, copper formate, copper propionate, copper oxyacetate, copper citrate, copper chloride, copper diammonium chloride, copper nitrate, copper carbonate, copper phosphate, copper pyrophosphate, copper disodium EDTA, copper diammonium EDTA, copper oxalate, copper tartrate, copper gluconate, copper glycinate, copper glutamate, copper aspartate, copper adipate, copper palmitate, copper stearate, copper caprylate, copper decanoate, copper undecylenate, copper neodecanoate, copper linoleate, copper oleate, copper borate, copper methanesulfonate, copper sulfamate, copper acetate, copper hydroxide, copper oxide, copper oxychloride-sulfate, copper sulfate, basic copper sulfate, copper-oxine, copper 3-phenylsalicylate, copper chloride hydroxide, copper dimethyldithiocarbamate, ammonium copper sulfate, copper magnesium sulfate, copper naphthenate, copper ethanolamine, chromated copper arsenate, ammoniacal copper arsenate, ammoniacal copper zinc arsenate, ammoniacal copper borate, Bordeaux mixture, copper zinc chromate, cufraneb, cupric hydrazinium sulfate, cuprobam, nano-copper materials, and copper didecyldimethylammonium chloride Algimycin P11-C, Aquatrine, A&V-70, Cutrine-plus, Stocktrine II and K-Tea algicide.

7. The synergistic mixture of claim 1, wherein $X_3$ is H or a halogen and $X_5$ is a halogen.

8. The synergistic mixture of claim 7, wherein, $X_3$ is Cl or Br and $X_4$ is H.

9. The synergistic mixture of claim 8, wherein, $R_1$ is H or $CH_3$.

10. The synergistic mixture of claim 9, wherein, $R_2$ is said substituted or unsubstituted 5-membered heterocyclic ring.

11. The synergistic mixture of claim 10, wherein, $R_2$ is the substituted furan or thiophene(thienyl) ring.

12. The synergistic mixture of claim 11, wherein, $R_2$ is the substituted or unsubstituted thiazole ring.

13. The synergistic mixture of claim 1, wherein $X_5$ and $X_6$ do not form the 6-membered aromatic fused ring consisting of carbon and hydrogen.

14. A method for controlling the growth of fungi, comprising the steps of:
contacting a fungi with a mixture of:
a source of copper; and
a hydrazone compound of Formula I:

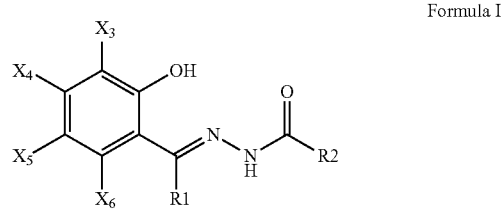

Formula I wherein $R_1$ is H, or $C_1$-$C_6$ alkyl;

$R_2$ is a substituted or unsubstituted 5- or 6-membered heteroaromatic, and a 5- or 6-membered saturated, or partially saturated heterocyclic ring whose members consist of carbon and at least one other atom chosen from O, N, or S which may optionally be fused with a second substituted or unsubstituted 5- or 6-membered aromatic, saturated, or partially saturated ring whose members consist of carbon or whose members consist of carbon and one or more other atoms chosen from 0, N, or S;

wherein said $R_2$ is selected from unsubstituted thiophene (thienyl); halogen substituted thiophene; alkyl substituted thiophene; unsubstituted furyl; halogen substituted furyl; alkyl substituted pyridyl; haloalkyl or alkyl substituted 1,3-thiazolyl; N-alkyl indolyl; hydroxyl, alkyl or haloalkyl substituted 1,2-diazoyl; alkyl plus phenyl substituted 1,2,3-triazolyl; phenyl substituted 1,2,3-thiadiazolyl; alkyl substituted piperidinyl; alkyl plus halogen substituted quinolinonyl;

$X_3$ is H, halogen, or $C_2$-$C_6$ alkenyl;

$X_4$ is H;

$X_5$ is H or halogen;

$X_6$ is H; and with the proviso that $X_5$ and $X_6$ may form a 6-membered aromatic fused ring consisting of carbon and hydrogen;

with the proviso that when said R2 is said unsubstituted thiopene(thienyl) then X5 is halogen or X5 and X6 form the 6-membered aromatic ring whose ring members consist of carbon or X3, X4, X5, X6, R1 are hydrogen or then X3 and X5 are halogen;

with the proviso that when said R2 is said halogen substituted thiophene then X3, X4, X5, and X6 are hydrogen, and R1 is selected from hydrogen and methyl or then X3 and X5 are halogen;

with the proviso that when said R2 is said alkyl substituted thiophene then X3, X4, X5, and X6 are hydrogen, and R1 is selected from hydrogen and methyl or then X3 and X5 are halogen;

with the proviso that when said R2 is said unsubstituted furyl then X5 is halogen;

with the proviso that when said R2 is said alkyl substituted furyl then X5 is halogen or hydrogen;

with the proviso that when said R2 is said halogen substituted furyl then X3 is alkenyl, with the proviso that when said R2 is said alkyl substituted pyridyl then X3 and X5 are halogen;

with the proviso that when said R2 is said haloalkyl or alkyl substituted 1,3-thiazole then X3 and X5 are halogen;

with the proviso that when said R2 is said alkyl substituted 1,3-thiazole then X3, X4, X5 and X6 are hydrogen and R1 is alkyl;

with the proviso that when said R2 is said N-alkyl indolyl then X5 is halogen;

with the proviso that when said R2 is said hydroxyl, alkyl or haloalkyl substituted 1,2-diazolyl then X3 and X5 are halogen;

with the proviso that when said R2 is said haloalkyl substituted 1,2-diazolyl then X3, X4, X5 and X6 are hydrogen and R1 is hydrogen or alkyl;

with the proviso that when said R2 is said hydroxyl substituted 1,2-diazolyl then X3, X4, X5 and X6 are hydrogen and R1 is alkyl;

with the proviso that when said R2 is said alkyl plus phenyl substituted 1,2,3-triazoyl then X3, X4, X5, X6 and R1 are hydrogen;

with the proviso that when R2 is said phenyl substituted 1,2,3-thiadiazolyl then X3, X4, X5, X6 and R1 are hydrogen;

with the proviso that when said R2 is said N-alkyl substituted piperidinyl then X3 and X5 are halogen;

with the proviso that when said R2 is said alkyl plus halogen substituted quinolinonyl then X4 and X6 are hydrogen; and wherein the copper and said compound of Formula I act synergistically to control the growth of fungi.

15. The method according to claim 14, wherein said fungi are plant pathogens.

16. The method according to claim 14 wherein the fungi are selected from the group consisting of: Ascomycete, Basidiomycete, Oomycete, and Deuteromycetei.

17. The method according to claim 16, wherein said fungi are selected from the group consisting of *Phytophthora* species, *Plasmopara viticola, Pseudoperonospora cubensis, Pythium* species, *Pyricularia oryzae, Colletotrichum* species, *Helminthosporium* species, *Alternaria* species, *Septoria nodorum, Leptosphaeria nodorum, Ustilago maydis, Erysiphe graminis, Puccinia* species, *Sclerotinia* species, *Sphaerotheca fuliginea, Cercospora* species, *Rhizoctonia* species, *Uncinula necator, Septoria tritici* and *Podosphaera leucotricha*.

* * * * *